(12) United States Patent
Stankus et al.

(10) Patent No.: US 7,824,601 B1
(45) Date of Patent: Nov. 2, 2010

(54) PROCESS OF MAKING A TUBULAR IMPLANTABLE MEDICAL DEVICE

(75) Inventors: John Stankus, Campbell, CA (US);
Syed F. A. Hossainy, Fremont, CA (US);
Jinping Wan, Sunnyvale, CA (US)

(73) Assignee: Abbott Cardiovascular Systems Inc., Santa Clara ( * ) Notice: Subject to any disclaimer, the term of this patent is extended or adjusted under 35 U.S.C. 154(b) by 67 days.

(21) Appl. No.: 11/940,158

(22) Filed: Nov. 14, 2007

(51) Int. Cl.
  *A61L 33/00* (2006.01)
  *B05D 1/06* (2006.01)
  *B29C 47/02* (2006.01)
  *B32B 1/08* (2006.01)

(52) U.S. Cl. .......... 264/465; 264/131; 264/171.12; 264/279; 427/2.24; 427/2.25; 427/180; 427/458

(58) Field of Classification Search .......... 264/131, 264/138, 145, 163, 171.12, 171.26, 279, 264/465; 427/2.24, 2.25, 180, 202, 206, 427/458

See application file for complete search history.

(56) References Cited

U.S. PATENT DOCUMENTS

| 2004/0030377 | A1* | 2/2004 | Dubson et al. ............. 623/1.13 |
| 2006/0226580 | A1* | 10/2006 | Xia et al. ..................... 264/465 |
| 2006/0264140 | A1* | 11/2006 | Andrady et al. ............. 442/341 |
| 2007/0016283 | A1* | 1/2007 | Greenhalgh et al. ........ 623/1.15 |
| 2007/0038290 | A1 | 2/2007 | Huang et al. |
| 2007/0055364 | A1 | 3/2007 | Hossainy et al. |
| 2007/0254012 | A1 | 11/2007 | Ludwig et al. |
| 2008/0033522 | A1* | 2/2008 | Grewe et al. ............... 623/1.11 |

OTHER PUBLICATIONS

U.S. Appl. No. 11/810,518, filed Jun. 5, 2007, Kramer-Brown.

* cited by examiner

Primary Examiner—Leo B Tentoni
(74) Attorney, Agent, or Firm—Squire, Sanders & Dempsey LLP (57) ABSTRACT

Medical devices, such as stents, including a fibrous layer including particles are disclosed. Methods of forming such medical devices using electrospinning are disclosed.

1 Claim, 9 Drawing Sheets

PROCESS OF MAKING A TUBULAR IMPLANTABLE MEDICAL DEVICE

BACKGROUND OF THE INVENTION

1. Field of the Invention

This invention relates to implantable medical devices and methods of fabricating that that have an electrospun fibrous network loaded with nanoparticles.

2. Description of the State of the Art

This invention relates to radially expandable endoprostheses, which are adapted to be implanted in a bodily lumen. An "endoprosthesis" corresponds to an artificial device that is placed inside the body. A "lumen" refers to a cavity of a tubular organ such as a blood vessel.

A stent is an example of such an endoprosthesis. Stents are generally cylindrically shaped devices, which function to hold open and sometimes expand a segment of a blood vessel or other anatomical lumen such as urinary tracts and bile ducts. Stents are often used in the treatment of atherosclerotic stenosis in blood vessels. "Stenosis" refers to a narrowing or constriction of the diameter of a bodily passage or orifice. In such treatments, stents reinforce body vessels and prevent restenosis following angioplasty in the vascular system. "Restenosis" refers to the reoccurrence of stenosis in a blood vessel or heart valve after it has been treated (as by balloon angioplasty, stenting, or valvuloplasty) with apparent success.

The treatment of a diseased site or lesion with a stent involves both delivery and deployment of the stent. "Delivery" refers to introducing and transporting the stent through a bodily lumen to a region, such as a lesion, in a vessel that requires treatment. "Deployment" corresponds to the expanding of the stent within the lumen at the treatment region. Delivery and deployment of a stent are accomplished by positioning the stent about one end of a catheter, inserting the end of the catheter through the skin into a bodily lumen, advancing the catheter in the bodily lumen to a desired treatment location, expanding the stent at the treatment location, and removing the catheter from the lumen.

In the case of a balloon expandable stent, the stent is mounted about a balloon disposed on the catheter. Mounting the stent typically involves compressing or crimping the stent onto the balloon. The stent is then expanded by inflating the balloon. The balloon may then be deflated and the catheter withdrawn. In the case of a self-expanding stent, the stent may be secured to the catheter via a constraining member such as a retractable sheath or a sock. When the stent is in a desired bodily location, the sheath may be withdrawn which allows the stent to self-expand.

The stent must be able to satisfy a number of mechanical requirements. First, the stent must be capable of withstanding the structural loads, namely radial compressive forces, imposed on the stent as it supports the walls of a vessel. Therefore, a stent must possess adequate radial strength. Radial strength, which is the ability of a stent to resist radial compressive forces, is due to strength and rigidity around a circumferential direction of the stent. Radial strength and rigidity, therefore, may also be described as, hoop or circumferential strength and rigidity.

Once expanded, the stent must adequately maintain its size and shape throughout its service life despite the various forces that may come to bear on it, including the cyclic loading induced by the beating heart. For example, a radially directed force may tend to cause a stent to recoil inward. Generally, it is desirable to minimize recoil. In addition, the stent must possess sufficient flexibility to allow for crimping, expansion, and cyclic loading. Longitudinal flexibility is important to allow the stent to be maneuvered through a tortuous vascular path and to enable it to conform to a deployment site that may not be linear or may be subject to flexure. Finally, the stent must be biocompatible so as not to trigger any adverse vascular responses.

The structure of a stent is typically composed of scaffolding that includes a pattern or network of interconnecting structural elements often referred to in the art as struts or bar arms. The scaffolding can be formed from wires, tubes, or sheets of material rolled into a cylindrical shape. The scaffolding is designed so that the stent can be radially compressed (to allow crimping) and radially expanded (to allow deployment). A conventional stent is allowed to expand and contract through movement of individual structural elements of a pattern with respect to each other.

Additionally, a medicated stent may be fabricated by coating the surface of either a metallic or polymeric scaffolding with a polymeric carrier that includes an active or bioactive agent or drug. Polymeric scaffolding may also serve as a carrier of an active agent or drug.

It may be desirable for a stent to be biodegradable or bioerodible. In many treatment applications, the presence of a stent in a body may be necessary for a limited period of time until its intended function of, for example, maintaining vascular patency and/or drug delivery is accomplished. Therefore, stents fabricated from biodegradable polymers can be configured to completely erode only after the clinical need for them has ended.

SUMMARY OF THE INVENTION

Various embodiments of the present invention include a tubular implantable medical device comprising: a tubular device body comprising a fibrous layer, the fibrous layer including a network of polymer fibers, the network of polymer fibers including a plurality of particles.

Further embodiments of the present invention include method of fabricating a tubular implantable medical device comprising: electrospinning polymer fibers to form a fibrous tubular layer comprising a fibrous network of the electrospun polymer fibers; and incorporating a plurality of polymer particles in the fibrous layer; and fabricating a device body from the fibrous layer with the incorporated polymer particles.

Additional embodiments of the present invention include a method of fabricating a tubular implantable medical device comprising: electrospinning a polymer fluid through a coaxial nozzle to form fibers of the polymer, the coaxial nozzle having an outer passageway containing the polymer fluid and an inner passageway containing particles, wherein at least some of the particles are encapsulated within the formed fibers upon exiting the nozzle and forming the fibers; and depositing the fibers over a tubular support to form a tubular fibrous layer.

Other embodiments of the present invention include a method of fabricating a tubular implantable medical device comprising: electrospinning a polymer fluid through a nozzle to form fibers of the polymer; depositing the fibers over a tubular support to form a tubular fibrous layer; and incorporating particles into the tubular fibrous layer.

DETAILED DESCRIPTION OF THE INVENTION

Various embodiments of the present invention include a tubular medical device including a device body including a layer of fibrous material. The fibrous layer can make up all or a majority of the device body. Alternatively, a device body can include a fibrous layer disposed over a non-fibrous layer. The fibrous material can be a network or polymer fibers which further includes a plurality of particles. In certain embodiments, the fibers, the particles, or both can include an active agent or drug for delivery to a vascular lumen upon implantation of the device.

Figure 1:
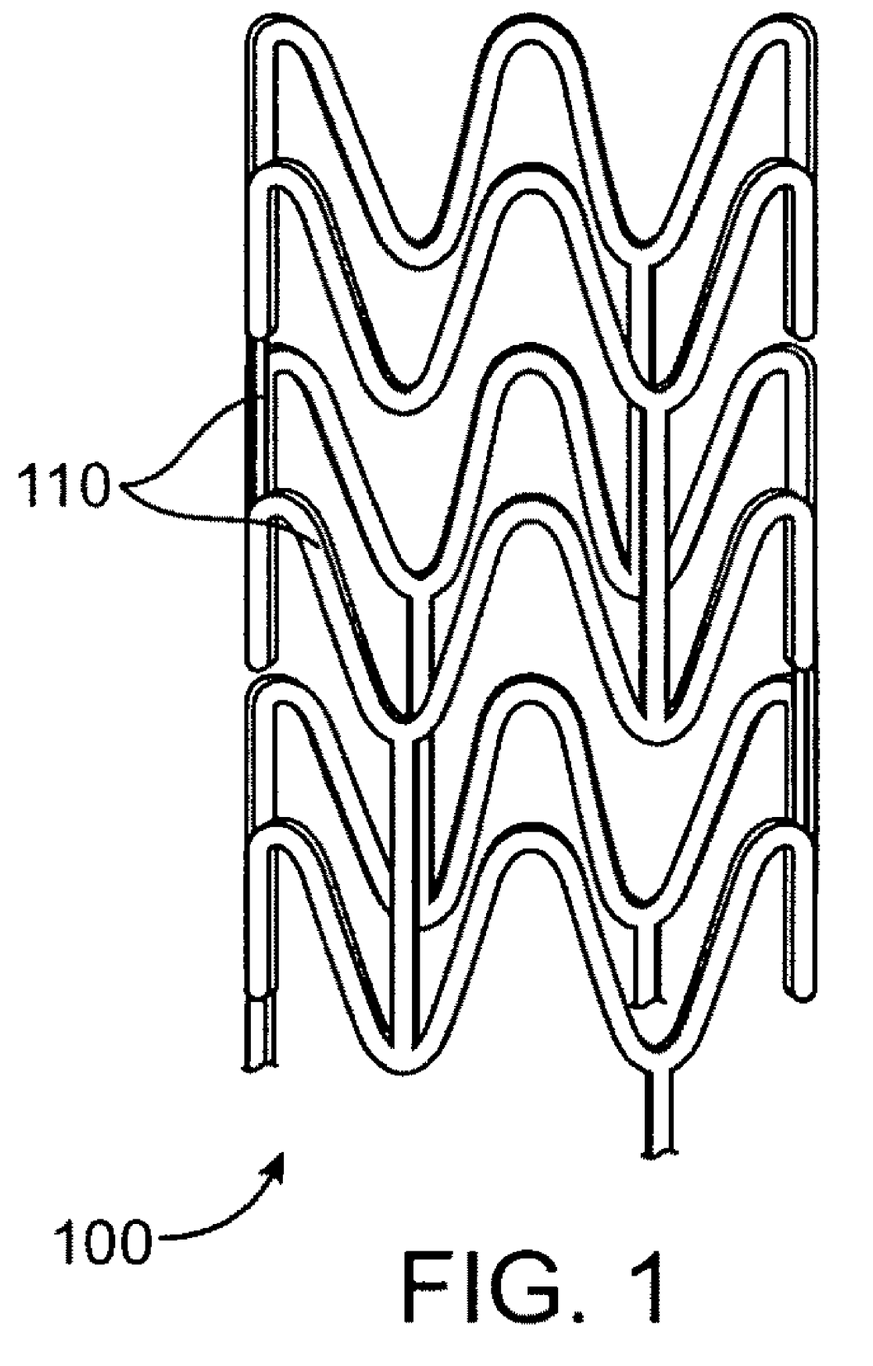
FIG. 1 depicts a view of a stent.

As used herein, a "medical device" includes, but is not limited to, self-expandable stents, balloon-expandable stents, stent-grafts, catheter balloons, drug-delivery balloons, and generally tubular medical devices. FIG. 1 depicts a view of a stent 100. In some embodiments, a stent may include a pattern or network of interconnecting structural elements 110. Stent 100 may be formed from a tube (not shown). Stent 100 includes a pattern of structural elements 110, which can take on a variety of patterns. The structural pattern of the device can be of virtually any design. The embodiments disclosed herein are not limited to stents or to the stent pattern illustrated in FIG. 1. The embodiments are easily applicable to other patterns and other devices. The variations in the structure of patterns are virtually unlimited. A stent such as stent 100 may be fabricated from a tube by forming a pattern in the tube with a technique such as laser cutting or chemical etching.

Figure 2:
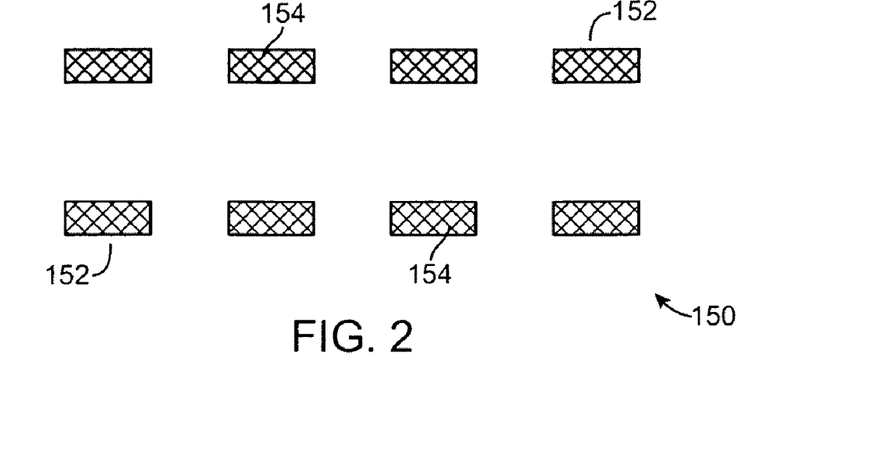
FIG. 2 depicts an axial cross-section of a stent body formed from a fibrous material.

In some embodiments, a tubular device body, such as a stent body or scaffolding, can be formed substantially or completely of a fibrous network or material that includes particles. In such embodiments, the body, scaffolding, or substrate of a stent body can be made from a fibrous network including particles. In this embodiment, a stent body, scaffolding, or substrate can refer to a stent structure with an outer surface to which no coating or layer of materials different from that of which the structure is manufactured. FIG. 2 depicts an axial cross-section of a stent 150 showing struts 152. Strut 152 is formed from a fibrous network or material 154 with particles (not shown).

In additional embodiments, a portion of the medical device can be made of the fibrous network with particles. In such embodiments, a tubular device body can be formed from at least one radial layer of the fibrous network with particles. These embodiments can include a layer of the fibrous network over a non-fibrous layer formed from a polymer or metal. The fibrous layer may be, for example, a luminal layer or abluminal layer of the device. In other embodiments, the fibrous layer may be a middle layer between non-fibrous luminal and abluminal layers.

Figure 3:
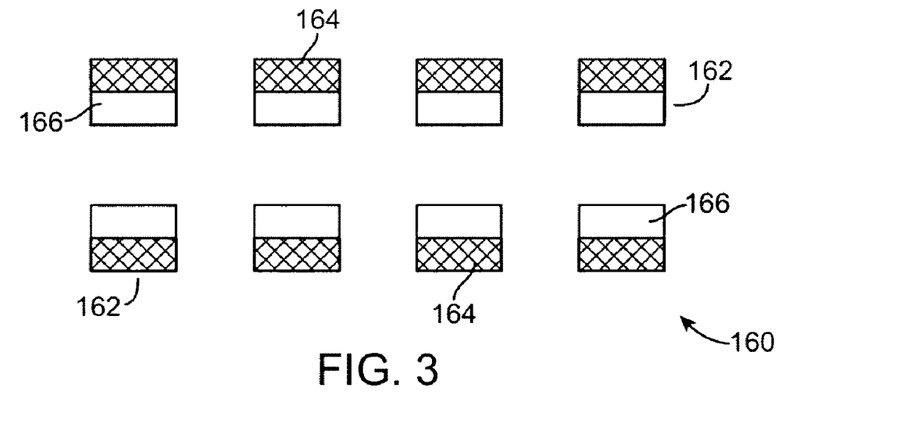
FIG. 3 depicts an axial cross-section of a stent with struts composed of a fibrous layer and a non-fibrous layer.
Figure 4:
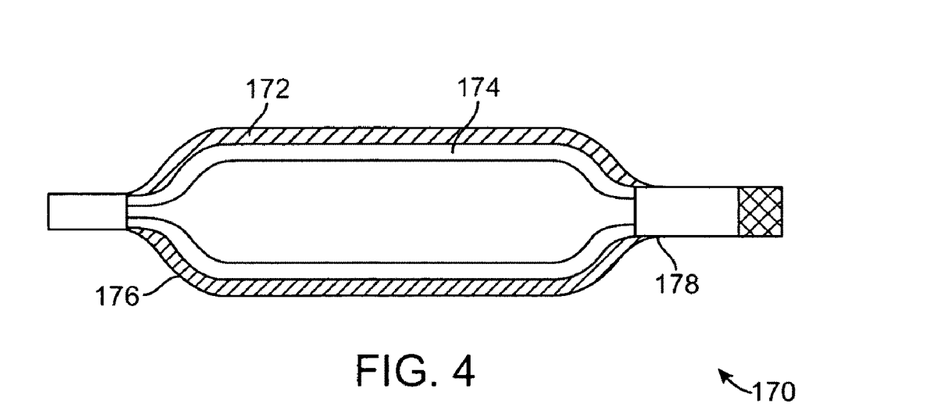
FIG. 4 depicts a balloon catheter assembly including a balloon having a fibrous layer mounted at an end of a catheter.

FIG. 3 depicts an axial cross-section of a stent 160 with struts 162. Struts 162 include an abluminal fibrous layer 164 and a luminal nonfibrous layer 166. Layer 166 can be a polymer or metal material. FIG. 4 depicts a balloon catheter assembly 170 including a balloon 176 mounted at an end of a catheter 178. Balloon 176 is composed of a balloon base layer 174 and a fibrous layer 172 disposed over the base layer. Base layer 174 may be composed of a polymer material typically used for fabricating balloons for use in vascular lumens, for example, Pebax from Arkema in Philadelphia, Pa. Balloon 176 is depicted in an expanded configuration to illustrate the layers.

In certain embodiments, the fibrous material is composed of a network of polymer fibers with particles included within the network. In some embodiments, a majority of the fibrous network may have fibers in an irregular or random arrangement. In one embodiment, the fibers can be arranged so that the axis of the fibers of the network generally follow or are generally parallel to the circumference of the tubular medical device. As is described in more detail below, the fibrous layer is formed by depositing electrospun fibers to form a tubular layer. The fibrous network is porous with regular irregular voids, spaces, or pores existing between the fibers of the network. The morphology or arrangement of the fiber axes can be random or partially ordered to form patterns.

Figure 5:
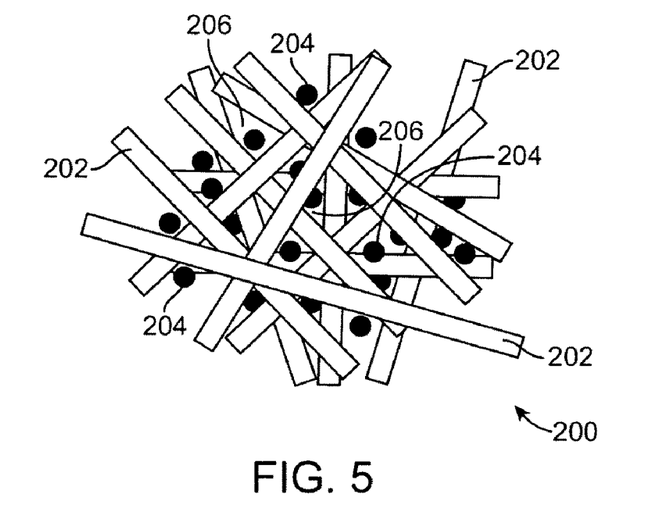
FIG. 5 depicts a schematic embodiment of a section of fibrous material that includes particles entrapped or dispersed within pores or voids between fibers.

In some embodiments, the particles can be entrapped within the pores or voids between the fibers of the fibrous network. As used herein, "entrapped" refers to particles positioned and held within voids existing between fiber strands and not within fiber strand material. FIG. 5 depicts a schematic embodiment of a section 200 of the fibrous material of fibers 202. Section 200 includes particles 204 entrapped within pores or voids 206 between fibers 202. In exemplary embodiments, the void fraction of the fibrous network is less than 20%, 20-50%, 50-85%, or greater than 85%.

Figure 6A:
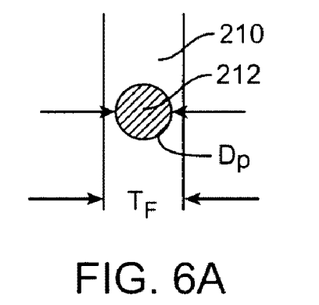
FIG. 6A depicts a schematic illustration of a fiber with a particle encapsulated within the fiber.
Figure 6B:
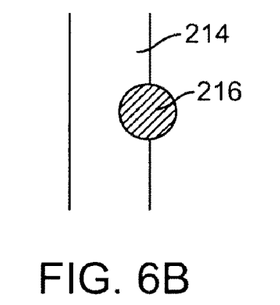
FIG. 6B depicts a schematic illustration of a particle partially encapsulated in a fiber.
Figure 6C:
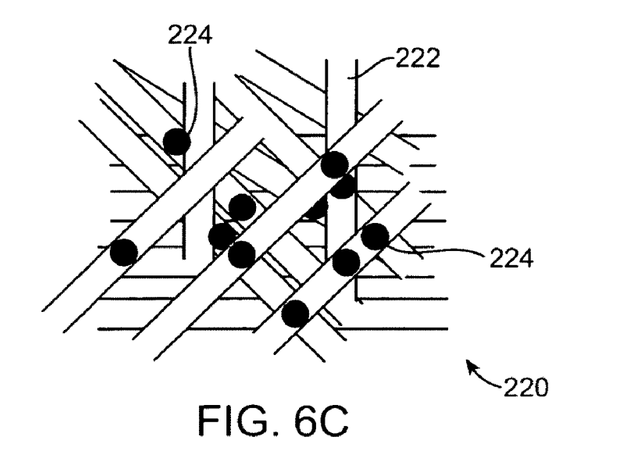
FIG. 6C depicts a schematic embodiment of a section of a fibrous material with particles encapsulated in fibers.

In other embodiments, the particles can be encapsulated or partially encapsulated within the polymer fibers. "Encapsulated" refers to a particle being completely enclosed within the material or volume of a fiber strand. "Partially encapsulated" refers to a particle in which part of the volume of the particle is enclosed within the fiber material or volume of a fiber strand and a part of the particles volume is outside and not enclosed within the fiber material or volume of the fiber strand. FIG. 6A depicts a schematic illustration of a fiber 210 with a particle 212 encapsulated within fiber 210. FIG. 6B depicts a particle 216 partially encapsulated in a fiber 214. FIG. 6C depicts a schematic embodiment of a section 220 of a fibrous material with particles 224 encapsulated in fibers 222. In some embodiments, a fibrous network can have particles both entrapped within the network and encapsulated within the fibers of a network.

In exemplary embodiments, the fibers can have a thickness, Tf, as shown in FIG. 6A, of less than 200 nm, 200-500 nm, 500-1000 nm, 1000-5000 nm, 5000-10000 nm, 10000-15000 nm, or greater than 15000 nm. Additionally, in exemplary embodiments, the average pore size of the fibrous material can be less than 500 nm, 500-1000 nm, 1000-10000 nm, 10-30 μm, 30-70 μm, 70-100 μm, or greater than 100 μm.

The size of the particles can be selected to allow encapsulation or entrapment. In particular, the sizes can be selected to be small enough to allow encapsulation in fibers of the fibrous network, as disclosed above, or small enough to fit within the pores of the fibrous network, as disclosed above. In exemplary embodiments, the particles can have characteristic size, such as a diameter Dp, as shown in FIG. 6A. In some embodiments, the particles can be nanoparticles. A nanoparticle refers to a particle with at least one dimension less than 100 nm. In exemplary embodiments, the average particles size can be less than 100 nm, 100-1000 nm, 1000-5000 nm, 5000-10000 nm, 10000-15000 nm, or greater than 15000 nm. Furthermore, the ratio of average void size to average particle size can be less than 2, 2-5, or greater than 5. The ratio of fiber thickness to average particle size can be less than 0.5, 0.5-1, 1-3, 3-5, or greater than 5.

Figure 7:
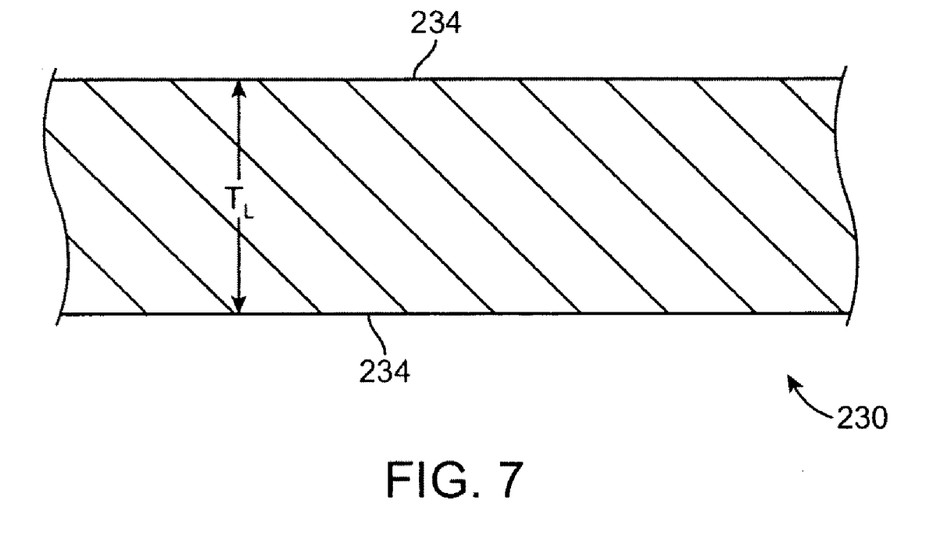
FIG. 7 depicts a close-up view of an axial cross-section of a section of a fibrous layer.

In further embodiments, the particles can be dispersed uniformly or nearly uniformly through a width of a layer of material or dispersed preferentially near a surface of the layer. FIG. 7 depicts a close-up view of an axial cross-section of a section 230 of a fibrous layer, for example from FIG. 2 or 3. Particles (not shown) can be distributed uniformly or nearly uniformly through thickness, $T_L$, of section 230. Alternatively, particles can be dispersed preferentially or exclusively at or near abluminal surface 232. Particles can also be dispersed preferentially or exclusively at or near luminal surface 234.

In some embodiments, the fibers of the fibrous network can be made partially or completely from a biodegradable, bioabsorbable, or biostable polymer. Biostable refers to polymers that are not biodegradable. The terms biodegradable, bioabsorbable, and bioerodible are used interchangeably and refer to polymers that are capable of being completely degraded and/or eroded when exposed to bodily fluids such as blood and can be gradually resorbed, absorbed, and/or eliminated by the body. The processes of breaking down and absorption of the polymer can be caused by, for example, hydrolysis and metabolic processes.

In general, functions performed by a stent, such as drug delivery and providing patency, are required only for a limited period of time. For example, a preferred or required treatment time by a stent may be less than 18 months, less than a year, between three and 12 months, or more narrowly, between four and eight months.

Exemplary polymers for use as fiber material include poly(L-lactide), poly(D,L-lactide), polyglycolide, polycaprolactone, polydioxanone, poly(trimethylene carbonate), poly(4-hydroxybutyrate), poly(ester amides) (PEA), polyurethanes, and copolymers thereof. In particular, poly(L-lactide-co-glycolide) can be used as a fiber material.

In some embodiments, the fibers and particles of the fibrous layer can have a coating with a synthetic or natural hydrogel. A hydrogel can include, but is not limited to, poly(ethylene glycol), poly(vinyl alcohol), polyvinylpyrrolidone, hyaluronan, collagen, gelatin, chitosan, alginate, aloe/pectin, cellulose, or polyNIPAAM. In further embodiments, the polymer fibers can be formed from such hydrogels. In additional embodiments, the hydrogel fibers can be crosslinked.

Additionally, the fibers can be formed from shape memory polymers so that the fibrous stent body exhibits shape memory effects. Exemplary shape memory polymers include block copolymers of poly(L-lactide) and polycaprolactone and polyurethanes, other biostable polyurethane copolymers, and polyurethane ureas. Shape memory polymers may also include polymers that possess appropriate thermal transition properties such as glass transition or soft segment melt temperatures that occur near or slightly (5-20° C.) above physiological temperature (37° C.).

In certain embodiments, the medical device can be designed for the localized delivery of a therapeutic agent. In some embodiments, the medical device can have a coating over a portion of the device that contains a therapeutic agent. In particular, the coating can be disposed over the fibrous layer. The coating can include a polymer carrier with a drug dispersed within carrier.

As discussed above, in further embodiments, the fibers, particles, or both can include an active agent or drug that can be released upon implantation of the medical device. In such embodiments, the active agent can be mixed or dispersed within the fiber material. The drug can be delivered through diffusion from fiber material into the patient. Alternatively, the drug may be delivered through degradation of the fiber material.

Additionally, as discussed above, the particles can include an active agent for delivery into the body of a patient. A drug can be encapsulated or dispersed within, adsorbed to the surface of or absorbed within the outside surface of the delivery particle. Alternatively, the delivery particle may be formed from a precipitate of a bioactive agent, e.g., by a neat bioactive agent or a salt of the bioactive agent with low solubility.

In some embodiments, the particles can provide for controlled release, sustained release, or both of active agent. Controlled release refers to delivery of an agent at a controlled rate for an extended time. Controlled release of a drug provides a well-characterized and reproducible dosage form. Sustained release refers to release of drug over an extended period of time. In sustained release, the rate and duration of drug are not necessarily designed to achieve a particular profile. A sustained release profile of an agent or drug can include zero-order release, exponential decay, step-function release, or other release profiles that carry over a period of time, for example, ranging from several hours to several years, from several days to several months, and from several days to several weeks. The terms "zero-order release", "exponential decay" and "step-function release" as well as other sustained release profiles are well known in the art (see, for example, Encyclopedia of Controlled Drug Delivery, Edith Mathiowitz, Ed., Culinary and Hospitality Industry Publications Services).

In some embodiments, the particles may be primarily or completely composed of a matrix material with active agents mixed, dispersed, or dissolved in the matrix material. The particle material can be a biostable or biodegradable polymer, metallic, or ceramic. Such particles may also be coated with an active agent. The drug in the matrix material may be delivered through diffusion through the matrix or degradation of the matrix material.

In other embodiments, the particles may encapsulate an active agent. Such particles can have an outer shell of polymer, metal, or ceramic with an inner compartment containing active agents. The shell can act as a release rate controlling layer. The core of the particles can be a reservoir of active agent or a drug-impregnated core of material. Particles may also include polymerosomes, micelles, vesicles, liposomes, glass (biodegradable and biostable), and micronized or nanoparticulate drug.

Representative classes of materials that may be used for particles include, but are not limited to, a biostable polymer; a bioabsorbable polymer; a biosoluble material; a biopolymer; a biostable metal; a bioerodible metal; a block copolymer of a bioabsorbable polymer or a biopolymer; a ceramic material such as a bioabsorbable glass; salts; fullerenes; lipids; carbon nanotubes; or a combination thereof.

Further embodiments of the present invention include fabricating a medical device having a fibrous polymeric layer with particles. In certain embodiments, a method of fabricating can include electrospinning polymer fibers to form a tubular layer that includes a fibrous network of the electrospun polymer fibers. The method further includes incorporating a plurality of polymer particles in the fibrous network of the electrospun polymer fibers.

Electrospinning refers to a process in which a high voltage is used to create an electrically charged jet of polymer fluid, such as a polymer solution or melt, which dries or solidifies to leave a polymer fiber. A system for electrospinning can include a syringe, a nozzle, a pump, a high-voltage power supply, and a grounded collector. An electrode is placed into the polymer fluid and the other can be attached to a grounded collector.

The polymer fluid is loaded into the syringe and the liquid is driven to the catheter tube tip by the syringe pump, forming a droplet at the tip. An electric field is subjected to the end of the catheter tube that contains the polymer fluid, which is held by its surface tension. The field induces a charge on the surface of the liquid. Mutual charge repulsion causes a force directly opposite to the surface tension.

As the intensity of the electric field is increased, a hemispherical surface of the fluid at the tip of the catheter tube elongates to form a conical shape known as the Taylor cone. With increasing field, a critical value is attained when the repulsive electrostatic force overcomes the surface tension and a charged jet of fluid is ejected from the tip of the Taylor cone. The jet is then elongated and whipped continuously by electrostatic repulsion until it is deposited on the grounded collector. Whipping due to a bending instability in the electrified jet and concomitant evaporation of solvent or solidification of melt (and, in some cases reaction of the materials in the jet with the environment) allow this jet to be stretched to diameters as small as nanometer-scale. The fiber tends to lay itself in an irregular or random fashion on the grounded collector.

The polymer solution or melt is contained in a glass tube, usually a pipette that is connected to a syringe like apparatus. A metering pump attached to the plunger of the syringe generates a constant pressure and flow of the fluid through the pipette. The driving force is provided by a high voltage source that can generate up to 30 kV, and the setup can be run on either positive or negative polarity. Adjusting the flow of the fluid and the magnitude of the electric field controls the fiber spinning rate.

Figure 8:
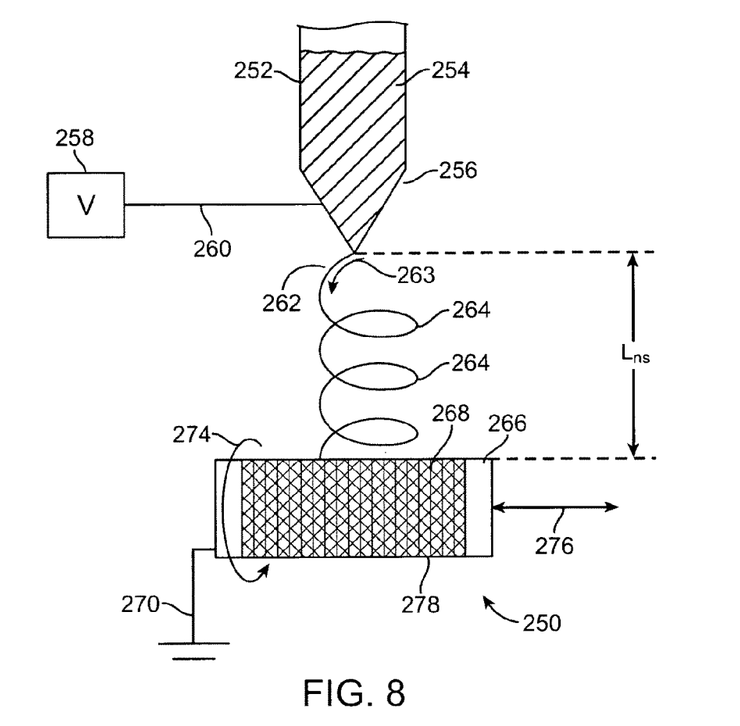
FIG. 8 depicts a schematic of an exemplary electrospinning process for fabricating a fibrous mesh with particles.

FIG. 8 depicts a schematic of an exemplary system 250 for fabricating a fibrous layer with particles. FIG. 8 shows a syringe 252 that contains a polymer fluid such as a melt or solution 254. A nozzle 256 which can be a needle, catheter tube, or pipette is in fluid communication with polymer fluid 254 in syringe 252. A high voltage power supply 258 is in electrical communication with polymer fluid 254 in nozzle 256, as shown by line 260. High voltage source 258 can be in electrical communication with polymer fluid 254 through a wire immersed in the fluid. A metering pump (not shown) attached to a plunger (not shown) of syringe 252 generates a constant pressure and flow of the fluid through nozzle 256.

A charged jet of fluid 262 is ejected from nozzle 256, as shown by an arrow 263, due to the pressure from the plunger. A spun fiber 264 is formed from the jet of fluid 262 as solvent in the jet evaporates or the polymer melt solidifies. Spun fiber 264 is deposited on a cylindrical support 266 to form a fibrous material 268. Support 266 is grounded as shown by grounding connection 270. Support 266 rotates, as shown by an arrow 274, and translates, as shown by arrow 276, to allow formation of a tubular fibrous layer 278. Support 266 can be a rotatable mandrel made from material, such as metal or Teflon® for a metal (e.g., stainless steel).

Alternatively, support member 266 can be a tubular polymeric or metallic construct on which the fibrous material adheres, thereby forming a fibrous layer or coating over the polymeric or metallic construct. The polymeric or metallic construct can be supported by rotatable mandrel to rotate support 266 during formation of tubular fibrous layer 278.

As described in more detail below, the particles can be incorporated into fibrous layer 268 is a several ways. In some embodiments, the particles can be sprayed from the same nozzle 256 as the polymer fluid and deposited on support 266. In other embodiments, the particles can be sprayed from a source separate from nozzle 256, for example, another nozzle. In additional embodiments, the particles can be positioned on the support prior to forming the fiber mesh. In further embodiments, the particles can be deposited on the fibrous mesh after its formation.

In the case of a polymer solution as the polymer fluid, exemplary solvents for use in the polymer solution include acetone, ethanol, ethanol/water mixtures, cyclohexanone, chloroform, hexafluoroisopropanol, 1,4-dioxane, tetrahydrofuran (THF), dichloromethane, acetonitrile, dimethyl sulfoxide (DMSO), N,N-dimethylformamide (DMF), N,N-dimethylacetamide (DMAC), cyclohexane, toluene, methyl ethyl ketone (MEK), xylene, ethyl acetate, and butyl acetate.

An electrospinning process has several process parameters that influence the properties of the formed fibrous material. Process parameters can include electrical potential, flow rate of polymer fluid from the nozzle, concentration of polymer in the fluid, distance between nozzle and the support member or collector, properties of the polymer fluid (e.g., viscosity, conductivity, surface tension), type of polymer, molecular weight of polymer, ambient conditions of process (temperature, humidity, and air velocity in the electrospinning chamber), and motion of the support member or collector.

The electrical potential can be a positive or negative polarity at the nozzle and the opposite polarity at the support or collector. In some embodiments, the support is not charged. The total electrical potential difference can be less than 20 V, 10-20 V, or greater than 20 V. For example, the nozzle can be +10 V and the support can be (−10) V.

For a polymer fluid that is a polymer solution, the concentration of polymer in a solvent of the polymer fluid can be less than 0.5 wt %, 0.5-1 wt %, 1-2 wt %, 2-4 wt %, 4-10 wt %, 10-15 wt %, 15-20 wt %, or greater than 20 wt %. In exemplary embodiments, the flow rate of fluid from the nozzle can be 0.1-0.5 ml/hr, 0.5-1 ml/hr, 1-2 ml/hr, 2-5 ml/hr, or greater than 5 ml/hr. The flow rate and concentration can be adjusted to obtain fibers of a desired thickness.

The distance between the nozzle and support (e.g., Lns in FIG. 8) can influence the solvent content or degree of solidification of fibers deposited on the support, which can affect the adhesion of deposited fibers to one another. As the formed fibers fall from the nozzle to the support, there is solidification or solvent evaporation from the formed fibers. Thus, the shorter the distance from the nozzle to the support, the lower is the degree of solidification or evaporation of solvent which can result in greater adhesion of fiber in a formed fibrous layer. The degree of solidification or evaporation also depends on the concentration of polymer in the polymer solution and the flow rate. The concentration, flow rate, and distance between the nozzle and support can be adjusted to obtain a desired degree of adhesion. For example, the distance may be adjusted so that deposited fibers have greater than less than 5 wt %, 5-10 wt %, 10-20 wt %, or greater than 20 wt % of solvent. The distance between the nozzle and the support member can be less than 6 cm, 6-10 cm, 10-15 cm, 15-20 cm, 20-30 cm, or greater than 30 cm.

In some embodiments, the electrospinning system can be enclosed in a chamber and conditions within the chamber can be controlled. The temperature in the chamber can be room temperature (20-30° C.) or greater than room temperature (20-30° C., 30-40° C., or greater than 40° C.). A higher temperature tends to increase the evaporation rate of a solvent in a polymer fluid and decrease the degree the solidification of a polymer melt.

The rotation rate of the support member can be less than 500 rpm, 500-2000 rpm, 2000-5000 rpm, 5000-15000 rpm, or greater than 15000 rpm.

Figure 9A:
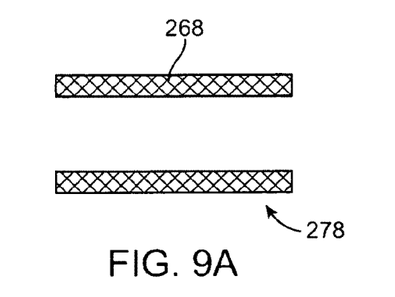
FIG. 9A depicts an axial cross-section of a fibrous tubular layer formed from the electrospinning process illustrated in FIG. 8.
Figure 9B:
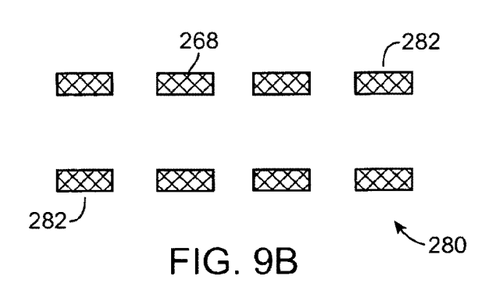
FIG. 9B depicts an axial cross-section of a stent body having a scaffolding composed of fibrous material which is formed by cutting a stent pattern into the fibrous tubular layer shown in FIG. 9A.

In some embodiments, a tubular body of a device can be formed from the tubular layer made from the electrospinning process. FIG. 9A depicts an axial cross-section of fibrous tubular layer 278 formed from the electrospinning process illustrated in FIG. 8. FIG. 9B depicts a stent body 280 having a scaffolding or struts 282 composed of fibrous material 268, formed by cutting a stent pattern into fibrous tubular layer 278 shown in FIG. 9A.

Figure 10A:
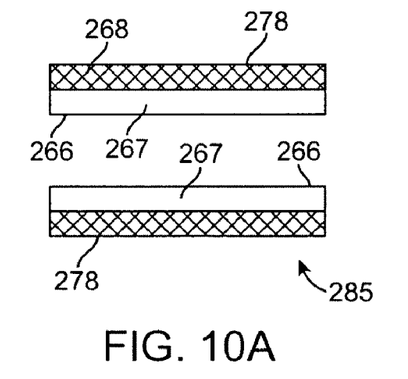
FIG. 10A depicts an axial cross-section of a layered tube composed of a fibrous tubular layer over a tubular construct.
Figure 10B:
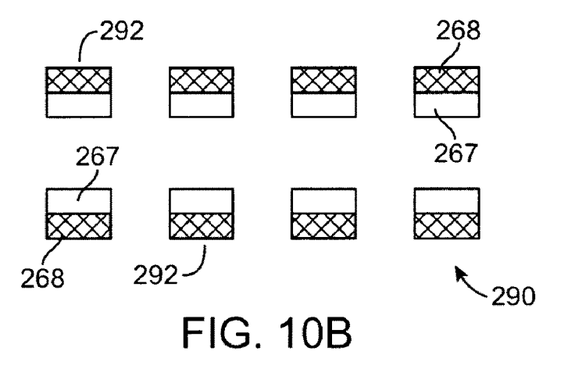
FIG. 10B depicts a stent body having a scaffolding composed of a layer of fibrous material and a tubular layer formed by cutting a stent pattern into the layered tube shown in FIG. 10A.

In other embodiments, a tubular device, such as stent 160 in FIG. 3 or balloon 170 in FIG. 3, can be formed with at least one fibrous layer formed from the electrospinning process. Balloon 170 can be formed by depositing electrospun fiber over a balloon, as shown in FIG. 8, with a balloon as the support member. FIG. 10A depicts an axial cross-section of a layered tube 285 that includes fibrous layer 278 formed over support 266, which corresponds to a tubular construct made from a non-fibrous construct material 267. FIG. 10B depicts a stent body 290 having a scaffolding or struts 292 composed of a layer of fibrous material 268 and a layer of construct material 267 formed by cutting a stent pattern into layered tube 285 shown in FIG. 10A.

As indicated above, particles can be incorporated in the fibrous layer in several ways. Additionally, particles can be incorporated into the fibrous layer during its formation or after its formation.

In some embodiments, the particles can be sprayed through the same nozzle as the polymer fluid. In other embodiments, the particles can be sprayed from a source separate from nozzle 256, for example, another nozzle. In additional embodiments, the particles can be positioned on the support prior to forming the fiber mesh. In further embodiments, the particles can be deposited on the fibrous mesh after its formation.

Figure 11:
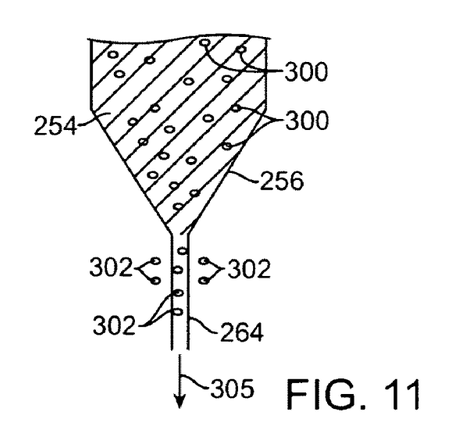
FIG. 11 depicts a close-up view of the nozzle from FIG. 8 containing particles dispersed in a polymer fluid.

In certain embodiments, the particles can be dispersed or suspended within the polymer fluid (e.g., polymer fluid 254 in FIG. 8) in the syringe and nozzle or the nozzle. In some embodiments, the suspension of polymer fluid and particles is sprayed from the nozzle. The particles may be encapsulated or partially encapsulated by fibers formed after exiting the nozzle. Alternatively, particles may be deposited without being encapsulated or partially encapsulated. Such particles may be entrapped within voids or pores between deposited fibers. FIG. 11 depicts a close-up view of nozzle 256 from FIG. 8 showing particles 300 dispersed in polymer fluid 254. A jet is ejected, as shown by an arrow 305, from nozzle 256, and forms fiber 264. Particles 304 can be encapsulated within the formed fiber 264. Particles 302 are not encapsulated or partially encapsulated in fiber 264.

For embodiments in which the polymer fluid is polymer solution, the solvent of the polymer solution can be selected to be a nonsolvent for particles. For example, PEA can be dissolved in ethanol together with a suspension of PLGA nanoparticles and electrospun. Alternatively, the solvent may be capable of swelling the particle material.

For embodiments in which the polymer fluid is a polymer melt, the temperature of the polymer melt can be less than the melting temperature ($T_m$) of the particle material to avoid melting of the particle. For example, polyglycolide particles ($T_m$=225-230° C., Medical Plastics and Biomaterials Magazine, March 1998), PLLA particles ($T_m$=173-178° C., Medical Plastics and Biomaterials Magazine, March 1998), or poly(4-hydroxybutyrate) particles ($T_m$=177° C., Science, Vol. 297 p. 803 (2002)) can be loaded within a polycaprolactone melt ($T_m$=58-63° C., Medical Plastics and Biomaterials Magazine, March 1998) to process particles within polycaprolactone fibers Alternatively, the temperature of the polymer melt may be above the melting temperature of the particle material, but the processing time and conditions allow deposition of the particle of a desired size.

Figure 12:
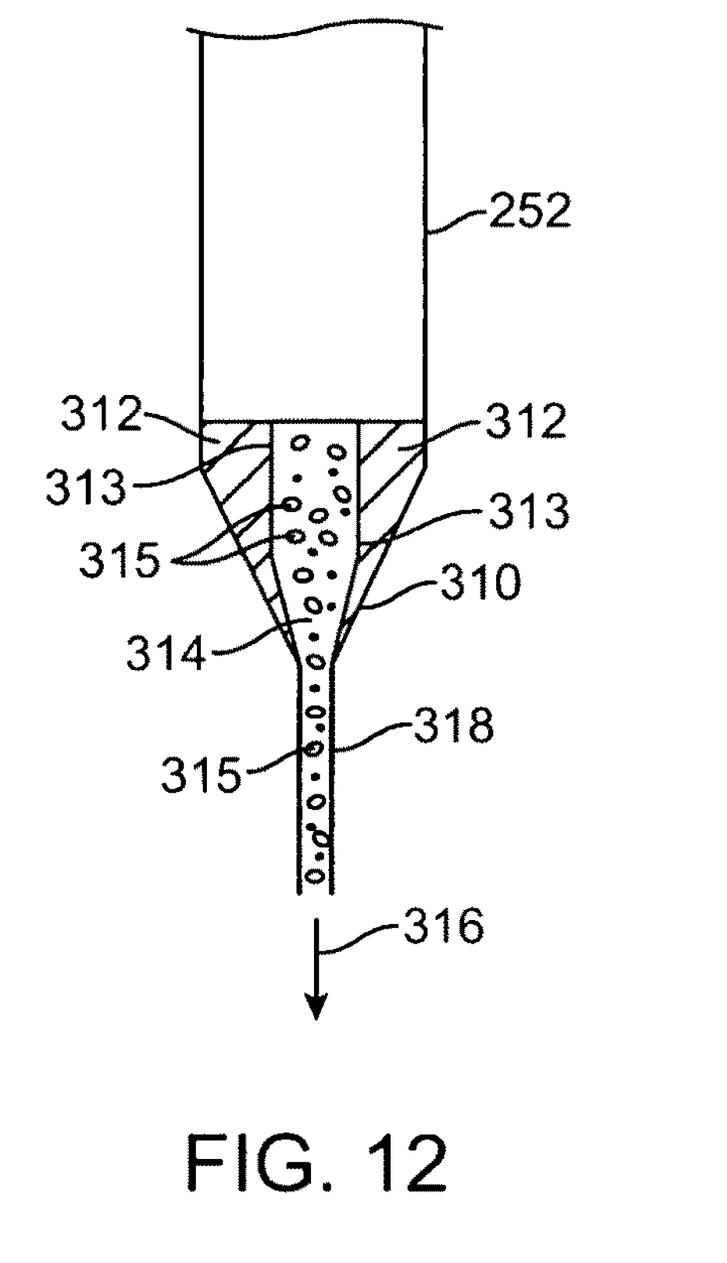
FIG. 12 depicts a cross-section of a coaxial nozzle for use in the electrospinning process depicted in FIG. 8.

In further embodiments, the polymer fluid and particles may be sprayed through a coaxial nozzle to facilitate encapsulation of the particles in the fiber. In such embodiments, a polymer fluid is ejected from a nozzle as a shell surrounding a core of particles. FIG. 12 depicts a cross-section of a coaxial nozzle 310 that has an outer passageway containing polymer fluid 312 and a wall 313 separating the outer passageway from an inner passageway containing a particle medium 314 including particles 315. The particles can be suspended free of any fluid or be suspended in a fluid. For example, the particles can be suspended in the same solvent as the polymer solution which is free of polymer. The particle medium can also be particles suspended in a polymer solution with the same polymer and solvent as in the outer passageway. The concentration of the polymer in the inner passageway polymer solution can be less, the same, or greater than the polymer solution in the outer passageway. As shown in FIG. 12, a jet 318 containing polymer fluid and particle medium is ejected from nozzle 310, as shown by an arrow 316, and forms a fiber that includes encapsulated particles.

Figure 13:
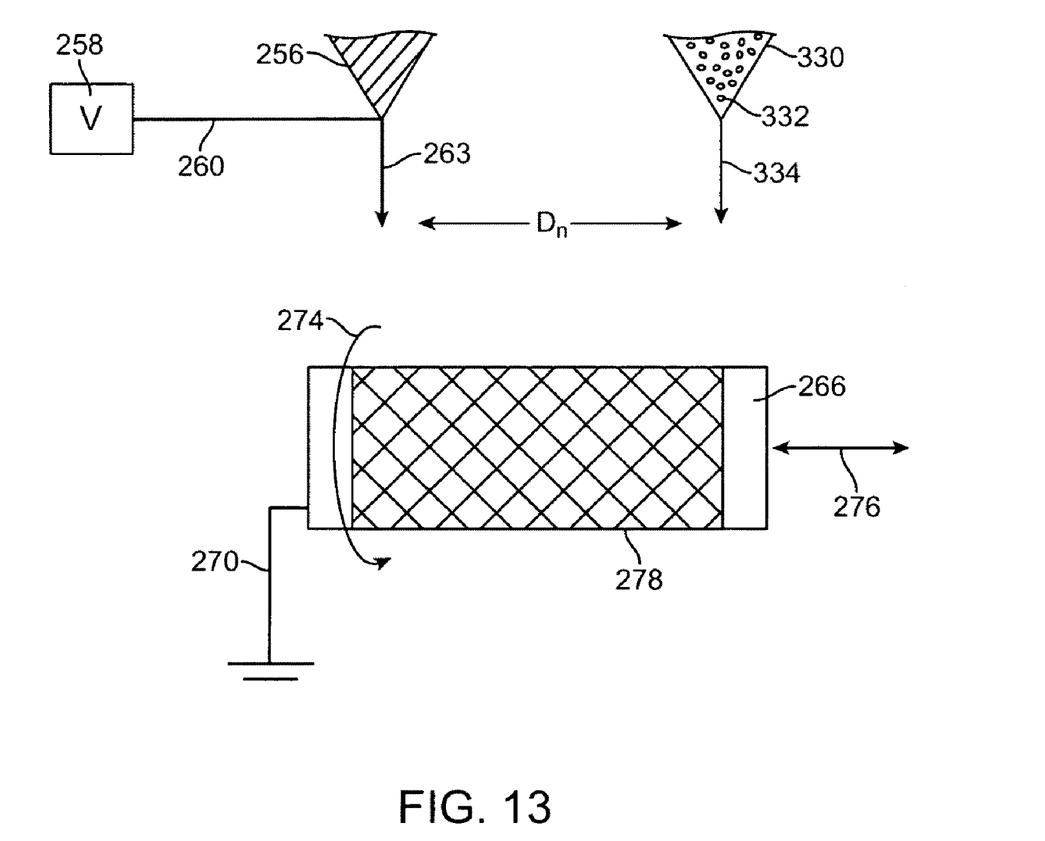
FIG. 13 depicts a system including a nozzle for forming fibers and a nozzle for spraying particles for depositing over a support.

In the embodiments of spraying particles and polymer fluid from the same nozzle, the concentration of polymer in the polymer solution can be adjusted to facilitate encapsulation. It is expected that increasing the concentration of polymer in the solution increases the degree and likelihood of encapsulation of particles in the fiber given an increase in fiber diameter.

In further embodiments, particles can be incorporated in the fibrous layer by spraying the particles from a nozzle separate from polymer fluid nozzle. FIG. 13 depicts a system including nozzle 256 for forming fibers and a nozzle 330 for spraying particles for depositing over support 266. Nozzle 330 includes a particle medium 332 that it sprays, as shown by an arrow 334, on fiber layer 278 that is formed on support member 266. Particle medium 332 can be particles free of fluid. Alternatively, particle medium 332 can be suspended in a fluid, such as the same solvent as the polymer solution.

In some embodiments, particle medium 330 can be connected to a high voltage source of the same polarity as polymer fluid 254 to facilitate deposition of the particles on support 266. In this case, the jet of polymer fluid and particles exiting the respective nozzles have the same charge. Thus, the particle stream and jet or fiber can repel one another, resulting in diversion of particles and fiber away from support 266. Thus, an axial distance Dn between the nozzles should be large enough to reduce or minimize the effect of the repulsion of the particles stream and jet. Alternatively, the particle stream and jet or fiber can be directed orthogonally. In a further variation, the nozzles can be positioned on opposite sizes of support member 266 so that the nozzles direct the particle stream and jet toward one another and onto support 266.

In additional embodiments of incorporating particles in a fibrous layer, the particles can be deposited on the support member prior to depositing the fibrous layer. Particles can be applied in a manner that they adhere to the support member. For example, the particles free of a fluid can be sprayed onto the support that has been wetted with a fluid, such as a solvent for the particle material. Alternatively, a fluid suspension of the particles can be sprayed on the support. For example, acetone swells, but does not dissolve PLLA. Solvents that swell and dissolve PLLA include chloroform, dichloromethane and hexafluoroisopropanol.

In further embodiments of incorporating particles in a fibrous layer, the particles can be deposited on the fibrous layer after its formation. Particles can be applied in a manner that they adhere to the fibrous layer. In some embodiments, the particles can be sprayed onto the support that has been wetted with a fluid. In one such embodiment, the fluid can be a nonsolvent for the fiber material that swells the fibers. The swelled fibers facilitate the adhesion of the particles to the fiber.

In another such embodiment, the fluid can be a solvent for the fiber material that partially dissolves the fiber material. In this case, the partially dissolved fiber may facilitate at least partial encapsulation of the particles in the partially dissolved fibers. Alternatively, a fluid suspension of the particles can be sprayed on the support that includes either a nonsolvent that swells the fibers or a solvent that can dissolve the fibers.

In other embodiments, the particles can be incorporated after fabricating a device body from the fibrous layer. In particular, a stent body can be formed as shown in FIGS. 9A-B and 10A-B, followed by application of particles, as described above.

In further embodiments, the polymer fibers can be electrospun from a suspension of particles of an aqueous solution of hydrogel. In such embodiments, the hydrogel fibers can be crosslinked. The crosslinked hyrogel fibers may then be swelled to encapsulate or increase the degree of encapsulation, or completely encapsulate the particles.

"Solvent" is defined as a substance capable of dissolving or dispersing one or more other substances or capable of at least partially dissolving or dispersing the substance(s) to form a uniformly dispersed solution at the molecular- or ionic-size level at a selected temperature and pressure. The solvent should be capable of dissolving at least 0.1 mg of the polymer in 1 ml of the solvent, and more narrowly 0.5 mg in 1 ml at the selected temperature and pressure, for example, ambient temperature and ambient pressure.

Representative examples of polymers that may be used to as a fiber material, particle material, or for a non-fibrous layer of a medical device include, but are not limited to, poly(N-acetylglucosamine) (Chitin), Chitosan, poly(hydroxyvalerate), poly(lactide-co-glycolide), poly(hydroxybutyrate), poly(hydroxybutyrate-co-valerate), polyorthoester, polyanhydride, poly(glycolic acid), poly(glycolide), poly(L-lactic acid), poly(L-lactide), poly(D,L-lactic acid), poly(L-lactide-co-glycolide); poly(D,L-lactide), poly(caprolactone), poly(trimethylene carbonate), polyethylene amide, polyethylene acrylate, poly(glycolic acid-co-trimethylene carbonate), co-poly(ether-esters) (e.g. PEO/PLA), polyphosphazenes, biomolecules (such as fibrin, fibrinogen, cellulose, starch, collagen and hyaluronic acid), polyurethanes, silicones, polyesters, polyolefins, polyisobutylene and ethylene-alphaolefin copolymers, acrylic polymers and copolymers other than polyacrylates, vinyl halide polymers and copolymers (such as polyvinyl chloride), polyvinyl ethers (such as polyvinyl methyl ether), polyvinylidene halides (such as polyvinylidene chloride), polyacrylonitrile, polyvinyl ketones, polyvinyl aromatics (such as polystyrene), polyvinyl esters (such as polyvinyl acetate), acrylonitrile-styrene copolymers, ABS resins, polyamides (such as Nylon 66 and polycaprolactam), polycarbonates, polyoxymethylenes, polyimides, polyethers, polyurethanes, rayon, rayon-triacetate, cellulose, cellulose acetate, cellulose butyrate, cellulose acetate butyrate, cellophane, cellulose nitrate, cellulose propionate, cellulose ethers, and carboxymethyl cellulose.

Additional representative examples of polymers that may be especially well suited for use as a fiber material, particle material, or for a non-fibrous layer material for a medical device according to the methods disclosed herein include ethylene vinyl alcohol copolymer (commonly known by the generic name EVOH or by the trade name EVAL), poly(butyl methacrylate), poly(vinylidene fluoride-co-hexafluoropropene) (e.g., SOLEF 21508, available from Solvay Solexis PVDF, Thorofare, N.J.), polyvinylidene fluoride (otherwise known as KYNAR, available from ATOFINA Chemicals, Philadelphia, Pa.), ethylene-vinyl acetate copolymers, and polyethylene glycol.

Representative examples of metallic materials or alloys that may be used for a non-fibrous layer of a medical device include, but are not limited to, cobalt chromium alloy (EL-GILOY), stainless steel (316L), high nitrogen stainless steel, e.g., BIODUR 108, cobalt chrome alloy L-605, "MP35N," "MP20N," ELASTINITE (Nitinol), tantalum, nickel-titanium alloy, platinum-iridium alloy, gold, magnesium, or combinations thereof. "MP35N" and "MP20N" are trade names for alloys of cobalt, nickel, chromium and molybdenum available from Standard Press Steel Co., Jenkintown, Pa. "MP35N" consists of 35% cobalt, 35% nickel, 20% chromium, and 10% molybdenum. "MP20N" consists of 50% cobalt, 20% nickel, 20% chromium, and 10% molybdenum.

For example, a stainless steel tube or sheet may be Alloy type: 316L SS, Special Chemistry per ASTM F138-92 or ASTM F139-92 grade 2. Special Chemistry of type 316L per ASTM F138-92 or ASTM F139-92 Stainless Steel for Surgical Implants in weight percent. An exemplary weight percent may be as follows: Carbon (C): 0.03% max; Manganese (Mn): 2.00% max; Phosphorous (P): 0.025% max.; Sulphur (S): 0.010% max.; Silicon (Si): 0.75% max.; Chromium (Cr): 17.00-19.00%; Nickel (Ni): 13.00-15.50%; Molybdenum (Mo): 2.00-3.00%; Nitrogen (N): 0.10% max.; Copper (Cu): 0.50% max.; Iron (Fe): Balance.

Drugs or therapeutic active agent(s) can include anti-inflammatories, antiproliferatives, and other bioactive agents.

An antiproliferative agent can be a natural proteineous agent such as a cytotoxin or a synthetic molecule. Preferably, the active agents include antiproliferative substances such as actinomycin D, or derivatives and analogs thereof (manufactured by Sigma-Aldrich 1001 West Saint Paul Avenue, Milwaukee, Wis. 53233; or COSMEGEN available from Merck) (synonyms of actinomycin D include dactinomycin, actinomycin IV, actinomycin $I_1$, actinomycin $X_1$, and actinomycin $C_1$), all taxoids such as taxols, docetaxel, and paclitaxel, paclitaxel derivatives, all olimus drugs such as macrolide antibiotics, rapamycin, everolimus, structural derivatives and functional analogues of rapamycin, structural derivatives and functional analogues of everolimus, FKBP-12 mediated mTOR inhibitors, biolimus, perfenidone, prodrugs thereof, co-drugs thereof, and combinations thereof. Representative rapamycin derivatives include 40-O-(3-hydroxy)propyl-rapamycin, 40-O-[2-(2-hydroxy)ethoxy]ethyl-rapamycin, or 40-O-tetrazole-rapamycin, 40-epi-(N1-tetrazolyl)-rapamycin (ABT-578 manufactured by Abbott Laboratories, Abbott Park, Ill.), prodrugs thereof, co-drugs thereof, and combinations thereof. In one embodiment, the anti-proliferative agent is everolimus.

An anti-inflammatory drug can be a steroidal anti-inflammatory agent, a nonsteroidal anti-inflammatory agent, or a combination thereof. In some embodiments, anti-inflammatory drugs include, but are not limited to, alclofenac, alclometasone dipropionate, algestone acetonide, alpha amylase, amcinafal, amcinafide, amfenac sodium, amiprilose hydrochloride, anakinra, anirolac, anitrazafen, apazone, balsalazide disodium, bendazac, benoxaprofen, benzydamine hydrochloride, bromelains, broperamole, budesonide, carprofen, ciclofrofen, cintazone, cliprofen, clobetasol propionate, clobetasone butyrate, clopirac, cloticasone propionate, cormethasone acetate, cortodoxone, deflazacort, desonide, desoximetasone, dexamethasone dipropionate, diclofenac potassium, diclofenac sodium, diflorasone diacetate, diflumidone sodium, diflunisal, difluprednate, diftalone, dimethyl sulfoxide, drocinonide, endrysone, enlimomab, enolicam sodium, epirizole, etodolac, etofenamate, felbinac, fenamole, fenbufen, fenclofenac, fenclorac, fendosal, fenpipalone, fentiazac, flazalone, fluazacort, flufenamic acid, flumizole, flunisolide acetate, flunixin, flunixin meglumine, fluocortin butyl, fluorometholone acetate, fluquazone, flurbiprofen, fluretofen, fluticasone propionate, furaprofen, furobufen, halcinonide, halobetasol propionate, halopredone acetate, ibufenac, ibuprofen, ibuprofen aluminum, ibuprofen piconol, ilonidap, indomethacin, indomethacin sodium, indoprofen, indoxole, intrazole, isoflupredone acetate, isoxepac, isoxicam, ketoprofen, lofemizole hydrochloride, lomoxicam, loteprednol etabonate, meclofenamate sodium, meclofenamic acid, meclorisone dibutyrate, mefenamic acid, mesalamine, meseclazone, methylprednisolone suleptanate, momiflumate, nabumetone, naproxen, naproxen sodium, naproxol, nimazone, olsalazine sodium, orgotein, orpanoxin, oxaprozin, oxyphenbutazone, paranyline hydrochloride, pentosan polysulfate sodium, phenbutazone sodium glycerate, pirfenidone, piroxicam, piroxicam cinnamate, piroxicam olamine, pirprofen, prednazate, prifelone, prodolic acid, proquazone, proxazole, proxazole citrate, rimexolone, romazarit, salcolex, salnacedin, salsalate, sanguinarium chloride, seclazone, sermetacin, sudoxicam, sulindac, suprofen, talmetacin, talniflumate, talosalate, tebufelone, tenidap, tenidap sodium, tenoxicam, tesicam, tesimide, tetrydamine, tiopinac, tixocortol pivalate, tolmetin, tolmetin sodium, triclonide, triflumidate, zidometacin, zomepirac sodium, aspirin (acetylsalicylic acid), salicylic acid, corticosteroids, glucocorticoids, tacrolimus, pimecorlimus, prodrugs thereof, co-drugs thereof, and combinations thereof. In one embodiment, the anti-inflammatory agent is clobetasol.

Alternatively, the anti-inflammatory may be a biological inhibitor of proinflammatory signaling molecules. Anti-inflammatory biological agents include antibodies to such biological inflammatory signaling molecules.

In addition, drugs or active can be other than antiproliferative agents or anti-inflammatory agents. These active agents can be any agent which is a therapeutic, prophylactic, or a diagnostic agent. In some embodiments, such agents may be used in combination with antiproliferative or anti-inflammatory agents. These agents can also have anti-proliferative and/or anti-inflammmatory properties or can have other properties such as antineoplastic, antiplatelet, anti-coagulant, anti-fibrin, antithrombonic, antimitotic, antibiotic, antiallergic, antioxidant, and cystostatic agents. Examples of suitable therapeutic and prophylactic agents include synthetic inorganic and organic compounds, proteins and peptides, polysaccharides and other sugars, lipids, and DNA and RNA nucleic acid sequences having therapeutic, prophylactic or diagnostic activities. Nucleic acid sequences include genes, antisense molecules which bind to complementary DNA to inhibit transcription, and ribozymes. Some other examples of other bioactive agents include antibodies, receptor ligands, enzymes, adhesion peptides, blood clotting factors, inhibitors or clot dissolving agents such as streptokinase and tissue plasminogen activator, antigens for immunization, hormones and growth factors, oligonucleotides such as antisense oligonucleotides and ribozymes and retroviral vectors for use in gene therapy. Examples of antineoplastics and/or antimitotics include methotrexate, azathioprine, vincristine, vinblastine, fluorouracil, doxorubicin hydrochloride (e.g. Adriamycin® from Pharmacia & Upjohn, Peapack N.J.), and mitomycin (e.g. Mutamycin® from Bristol-Myers Squibb Co., Stamford, Conn.). Examples of such antiplatelets, anticoagulants, antifibrin, and antithrombins include sodium heparin, low molecular weight heparins, heparinoids, hirudin, argatroban, forskolin, vapiprost, prostacyclin and prostacyclin analogues, dextran, D-phe-pro-arg-chloromethylketone (synthetic antithrombin), dipyridamole, glycoprotein IIb/IIIa platelet membrane receptor antagonist antibody, recombinant hirudin, thrombin inhibitors such as Angiomax ä (Biogen, Inc., Cambridge, Mass.), calcium channel blockers (such as nifedipine), colchicine, fibroblast growth factor (FGF) antagonists, fish oil (omega 3-fatty acid), histamine antagonists, lovastatin (an inhibitor of HMG-CoA reductase, a cholesterol lowering drug, brand name Mevacor® from Merck & Co., Inc., Whitehouse Station, N.J.), monoclonal antibodies (such as those specific for Platelet-Derived Growth Factor (PDGF) receptors), nitroprusside, phosphodiesterase inhibitors, prostaglandin inhibitors, suramin, serotonin blockers, steroids, thioprotease inhibitors, triazolopyrimidine (a PDGF antagonist), nitric oxide or nitric oxide donors, super oxide dismutases, super oxide dismutase mimetic, 4-amino-2,2,6,6-tetramethylpiperidine-1-oxyl (4-amino-TEMPO), estradiol, anticancer agents, dietary supplements such as various vitamins, and a combination thereof. Examples of such cytostatic substance include angiopeptin, angiotensin converting enzyme inhibitors such as captopril (e.g. Capoten® and Capozide® from Bristol-Myers Squibb Co., Stamford, Conn.), cilazapril or lisinopril (e.g. Prinivil® and Prinzide® from Merck & Co., Inc., Whitehouse Station, N.J.). An example of an antiallergic agent is permirolast potassium.

Other therapeutic substances or agents which may be appropriate include alpha-interferon, and genetically engineered epithelial cells. The foregoing substances are listed by way of example and are not meant to be limiting.

Other bioactive agents may include antiinfectives such as antiviral agents; analgesics and analgesic combinations; anorexics; antihelmintics; antiarthritics, antiasthmatic agents; anticonvulsants; antidepressants; antidiuretic agents; antidiarrheals; antihistamines; antimigrain preparations; antinauseants; antiparkinsonism drugs; antipruritics; antipsychotics; antipyretics; antispasmodics; anticholinergics; sympathomimetics; xanthine derivatives; cardiovascular preparations including calcium channel blockers and beta-blockers such as pindolol and antiarrhythmics; antihypertensives; diuretics; vasodilators including general coronary; peripheral and cerebral; central nervous system stimulants; cough and cold preparations, including decongestants; hypnotics; immunosuppressives; muscle relaxants; parasympatholytics; psychostimulants; sedatives; tranquilizers; naturally derived or genetically engineered lipoproteins; and restenoic reducing agents. Other active agents which are currently available or that may be developed in the future are equally applicable.

EXAMPLES

The examples set forth below are for illustrative purposes only and are in no way meant to limit the invention. The following examples are given to aid in understanding the invention, but it is to be understood that the invention is not limited to the particular materials or procedures of examples.

Example 1

Figure 14:
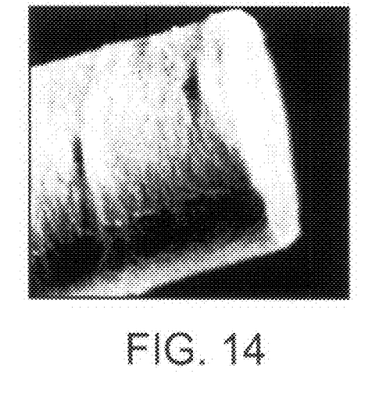
FIG. 14 depicts an image of an electrospun PLLA conduit or tube.

2 wt % of high inherent viscosity PLLA in hexafluoroisopropanol was electrospun utilizing voltages of +10 kV (nozzle) and −10 kV (mandrel), a flowrate of 1 mL/hr, over a distance of 10 cm onto a 4.0 mm stainless steel mandrel rotating at 3000 rpm for 30 min. This PLLA 4.0 mm inner diameter fibrous tube was then annealed at 55° C. overnight on the mandrel in a vacuum oven to remove residual solvent. FIG. 14 depicts an image of the electrospun PLLA conduit or tube.

Example 2

Figure 15:
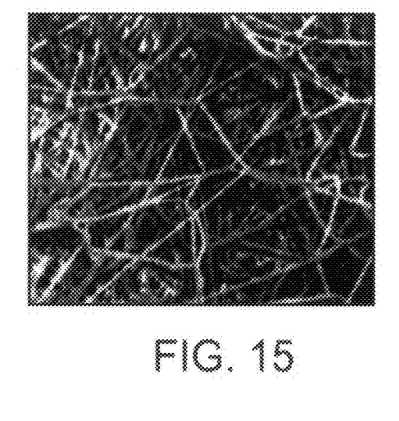
FIG. 15 depicts the surface structure of an electrospun PLLA conduit image from scanning electron microscopy (SEM).

A PLLA electrospun tube segment was cut and placed on carbon tape, sputter coated with gold-palladium and then imaged by scanning electron microscopy. Surface morphology consists of micron and sub-micron diameter fibers layered on one another. FIG. 15 depicts the surface structure of the electrospun PLLA conduit image from scanning electron microscopy (SEM).

Example 3

Figure 16A:
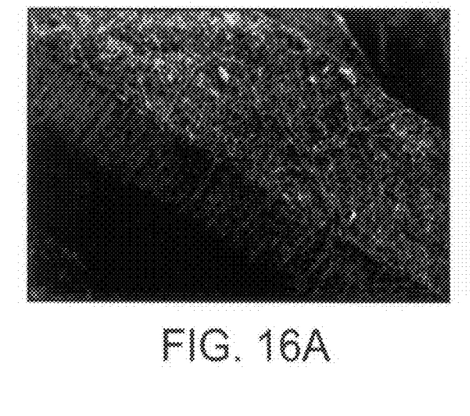
FIGS. 16A-C depicts fiber morphology of a laser cut implant.
Figure 16B:
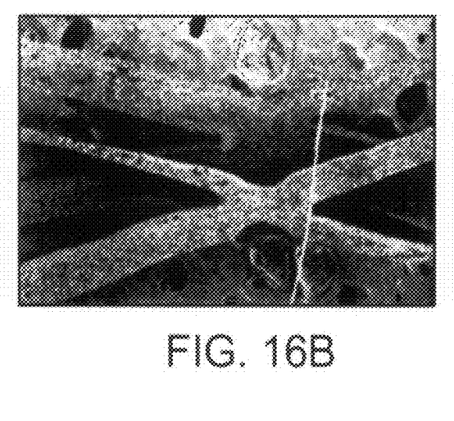
Figure 16C:
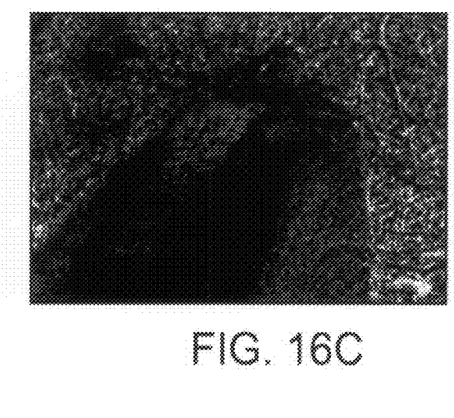

The PLLA 4.0 mm conduit of Examples 1-2 was laser cut. Retained fiber morphology was examined by scanning electron microscopy. FIGS. 16A-C depicts retained fiber morphology the laser cut implant.

Example 4

Figure 17:
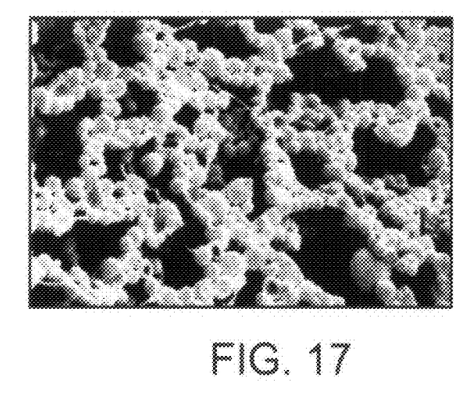
FIG. 17 depicts an SEM image of approximately 200 nm PLGA nanoparticles loaded with ApoA1 mimetic peptide.

FIG. 17 depicts an SEM image of ~200 nm PLGA nanoparticles loaded with Apolipoprotein A-1 (ApoA1) mimetic peptide. ApoA1 is an apolipoprotein and is the major protein component of high density lipoprotein (HDL) in plasma. It has been found the mimetic peptide functions similarly as the wild-type ApoA1 protein.

While particular embodiments of the present invention have been shown and described, it will be obvious to those skilled in the art that changes and modifications can be made without departing from this invention in its broader aspects. Therefore, the appended claims are to encompass within their scope all such changes and modifications as fall within the true spirit and scope of this invention.

What is claimed is:
1. A method of fabricating a tubular implantable medical device comprising:
   electrospinning a polymer fluid through a coaxial nozzle to form fibers of the polymer, the coaxial nozzle having an outer passageway containing the polymer fluid and an inner passageway containing biodegradable polymer particles, wherein at least some of the particles are encapsulated within the formed fibers upon exiting the nozzle and forming the fibers;
   depositing the fibers over a tubular support to form a tubular fibrous layer; and
   forming a stent from the tubular fibrous layer.

* * * * *